United States Patent [19]

Noda

[11] Patent Number: 5,572,322
[45] Date of Patent: Nov. 5, 1996

[54] APPARATUS FOR MEASURING PARTICLE PROPERTIES

[75] Inventor: Kazutoshi Noda, Tsukuba, Japan

[73] Assignee: Agency of Industrial Science & Technology, Ministry of International Trade & Industry, Tokyo, Japan

[21] Appl. No.: 404,438

[22] Filed: Mar. 15, 1995

[30] Foreign Application Priority Data

Jun. 29, 1994 [JP] Japan .................................. 6-147263

[51] Int. Cl.⁶ ................................................ G01N 21/00
[52] U.S. Cl. ......................... 356/338; 356/343; 356/455; 356/72; 356/73; 73/580
[58] Field of Search ................................... 356/338, 343, 356/72, 73, 336, 38, 36, 445; 73/580

[56] References Cited

U.S. PATENT DOCUMENTS

| | | | |
|---|---|---|---|
| 4,896,961 | 1/1990 | Ito | 356/73 |
| 4,928,153 | 5/1990 | Glass | 356/343 |
| 5,296,910 | 3/1994 | Cole | 356/28.5 |
| 5,481,357 | 1/1996 | Alsán | 356/338 |

*Primary Examiner*—Frank Gonzalez
*Assistant Examiner*—Reginald A. Ratliff
*Attorney, Agent, or Firm*—Oblon, Spivak, McClelland, Maier & Neustadt, P.C.

[57] ABSTRACT

An apparatus measures the diameter, relative concentration and weight of particles. The detection of scattered light produced when light is projected at particles drawn into a nozzle-shaped measuring space is used to measure particle diameter, particle concentration is measured based-on variations in the intensity of transmitted light, and particle weight is measured based on changes in operating frequency of a crystal oscillator resulting from the adhesion of particles on the surface of the crystal oscillator.

4 Claims, 2 Drawing Sheets

APPARATUS FOR MEASURING PARTICLE PROPERTIES

BACKGROUND OF THE INVENTION

1. Field of the Invention

The present invention relates to an apparatus that enables non-contact measurement of particle properties, and more particularly to an apparatus that enables real-time, simultaneous, non-contact measurement of the size, relative concentration and weight of particles without adversely affecting particle characteristics.

2. Description of the Prior Art

Conventionally, the weight, relative concentration and size (diameter) of particles have been measured using a specialized device for each type of measurement. Since the particles that each measurement system take in are not the same, even though a particular particle sample may provide relative concentration data, it may be impossible to measure the size of particles in the sample. Thus, while it may be possible to clarify one type of measurement data, it has not been possible to clarify relationships between the various types of measurement data. Also, particle weight is measured by first capturing the particles on filter paper or the like, and then using a standard gravimeter. This means that particle weight cannot be measured in real-time, and the measurement takes time and lacks good precision. To try to achieve even slightly better precision it has been necessary to use a larger suction pump to increase the suction quantity, but this increases the size of the measurement apparatus and its electrical power consumption.

An object of the present invention is to provide an apparatus that enables real-time, simultaneous measurement of the size, relative concentration and weight of particles.

SUMMARY OF THE INVENTION

To attain the above object, the present invention provides an apparatus for measuring particle properties, comprising a first measurement section having a nozzle-shaped configuration for light incidence, said first measurement section having an inside diameter that does not allow the simultaneous passage of multiple particles; a second measurement section that is connected to the first measurement section and is able to transmit light; a third measurement section that is connected to the second measurement section, said third measurement section having a particle adhesive on its surface and an internal crystal oscillator; intake means for guiding airborne particles to the third measurement section via the first and second measurement sections; a first optical system that projects light at the first measurement section and receives light scattered from particles in the first measurement section; and a second optical system that projects light at the second measurement section and receives light transmitted between particles in the second measurement section; wherein particle size is measured based on intensity of scattered light received by the first measurement section, relative concentration of particles is measured based on intensity of transmitted light received by the second measurement section, and particle weight is measured based on amplitude of variation in operating frequency of the crystal oscillator to which particles have adhered in the third measurement section.

As described above, in the apparatus for measuring particle properties according to the present invention which has three measurement sections that are interconnected, the size, relative concentration and weight of particles are simultaneously measured while the particles are being supplied, so measured values are inter-related and highly accurate. The invention measures particle properties based principally on information contained in light scattered, transmitted and reflected by particles. This makes it possible to readily measure such properties on a real-time basis. Moreover, the measurement apparatus of this invention can readily be compactly fabricated, and as it does not produce any electrical sparking, it is safe to use in a combustible gas environment.

The above and other features of the present invention will become apparent from the following description made with reference to the drawings.

DESCRIPTION OF THE PREFERRED EMBODIMENTS

Figure 1:
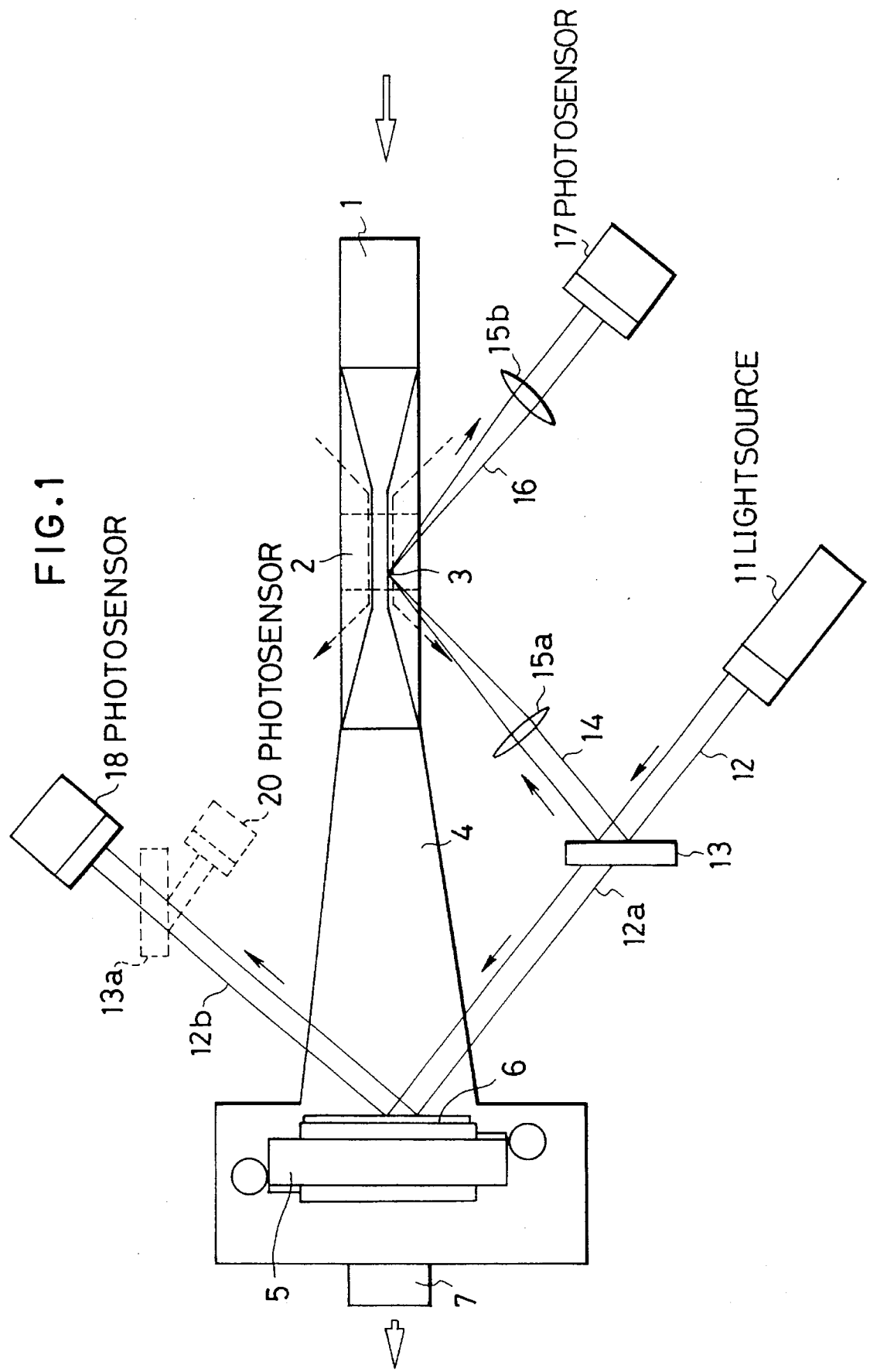
FIG. 1 is a drawing illustrating the configuration of an embodiment of the apparatus for measuring particle properties according to the invention.

An embodiment of the invention will now be described with reference to the drawings. The illustrated apparatus for measuring particle properties is comprised of a particle intake section 1, a particle diameter measuring cell 2 constituting a first measurement section, a light spot 3 used for particle diameter measurement, a measuring cell 4 having second and third measurement sections for measuring the weight and relative concentration of particles, a crystal oscillator 5, particle adhesive 6, an exhaust port 7 connected to a pump or other such intake means (not shown), a light source 11, a light beam 12, a semi-reflecting mirror 13, a light beam 14 used in the measurement of particle diameter, lenses 15a and 15b, a photosensor 17 used in the measurement of particle diameter, a photosensor 18 used in the measurement of relative concentration, a mirror 19 used in the measurement of relative concentration, and a photosensor 20 used for measuring the frequency of the crystal oscillator. Reference numeral 16 denotes scattered light.

Typical examples of the types of particles that might be subjected to measurement by the apparatus of this invention are carbon particles found in mines and tunnels, and dust particles found in factories. Airborne particles to be measured are drawn into the apparatus via the particle intake section 1. Connected to the particle intake section 1 is the particle diameter measuring cell 2, which has a thin, cylindrical nozzle-shaped configuration having a funnel-shaped intake section at one end and a funnel-shaped exhaust section at the other end to separate entrained particles into individual particles. The inside of the measuring cell 2 is of a diameter that does not allow the simultaneous passage of multiple particles. The measuring cell 2 is arranged so that the light beam 14 used in the measurement of particle diameter, as described below, impinges on the cell 2, illuminating one particle at a time in the light spot 3. This light reflected (scattered) by each particle has an intensity that varies according to the size (diameter) of the particle. This scattered light 16 is directed to the particle diameter measurement photosensor 17. While the measuring cell 2 may be of any conventional shape and material, it is preferable to use a cell of quartz having good transmissivity and a low degree of light frequency dependence.

The diameter and configuration of the opening of the particle intake section 1 may be selected according to the particles to be measured. Depending on the diameter of the particles to be measured, the opening may be provided with a known filter such as a slit or the like that prevents the entry of particles over a certain diameter. The optical system used for measuring particle diameter is configured so that light emitted from the light source 11 is formed into a light beam 12 by an associated lens or lenses (not shown). This light beam 12 is separated by the semi-reflecting mirror 13 into one light beam 14 that is projected onto the particle diameter measuring cell 2 via lens 15a, and another light beam 12a that is used for measuring the relative concentration of particles. The lens 15a focusses the light beam 14 to a light spot 3 on the measuring cell 2 in which particles are illuminated one at a time. The intensity of the scattered light from each particle thus illuminated corresponds to the diameter of the particle. This scattered light is focussed onto the photosensor 17 by lens 15b.

The light source 11 may be constituted by a gas laser, light-emitting diode, halogen lamp, or any other known light source means. However, it is preferable to use a small, light semiconductor laser. A conventional semi-reflecting mirror and lenses may be used for the semi-reflecting mirror 13 and lenses 15a and 15b. A beam-splitter may be used instead of a semi-reflecting mirror, and the lens does not have to be configured as a single concave lens but may be a lens system comprised of a plurality of lenses. The photosensor 17 may be a conventional photodiode, photomultiplier or the like. A PIN photodiode or avalanche photodiode is particularly suitable as such photodiodes are small and light, have low power dissipation and do not produce electrical sparks. The photosensor 17 produces an output corresponding to a scattered light intensity that varies depending on the particle diameter. This intensity output is normally generated as an electrical signal that is processed, displayed, subjected to precision compensation and the like by means of known specialized electrical circuits, using instruments such as optical power meters, computers, counters, oscillographs, and so forth.

The position of the light spot 3 in the measuring cell 2 is fixed at a point at which the intensity of the scattered light output is at its highest. The diameter of each of the particles is thus measured without contact with the particles, and the particles thus measured are then drawn into the measuring cell 4 for measuring the weight and relative concentration of the particles. The measuring cell 2 does not have to have the configuration shown in FIG. 1, and may be of any configuration that ensures good input of light beam 14 and output of scattered light 16.

Light beam 12a passes through the measuring cell 4 and is reflected by a surface of the crystal oscillator 5 configured to reflect light. This gives rise to reflected light 12b, which passes out from the measuring cell 4 and impinges on the photosensor 18 used for measuring the relative concentration of particles. It is arranged so that between the entry of light beam 12a into measuring cell 4 and the exit from measuring cell 4 of the light 12b reflecting from the surface of the crystal oscillator 5, the light passes between particles that have entered the measuring cell 4 after passing through the measuring cell 2. As the intensity of transmitted light varies depending on the concentration of the particles, the relative concentration of the particles can be measured by measuring the degree of this variation in the intensity of the light.

Figure 2:
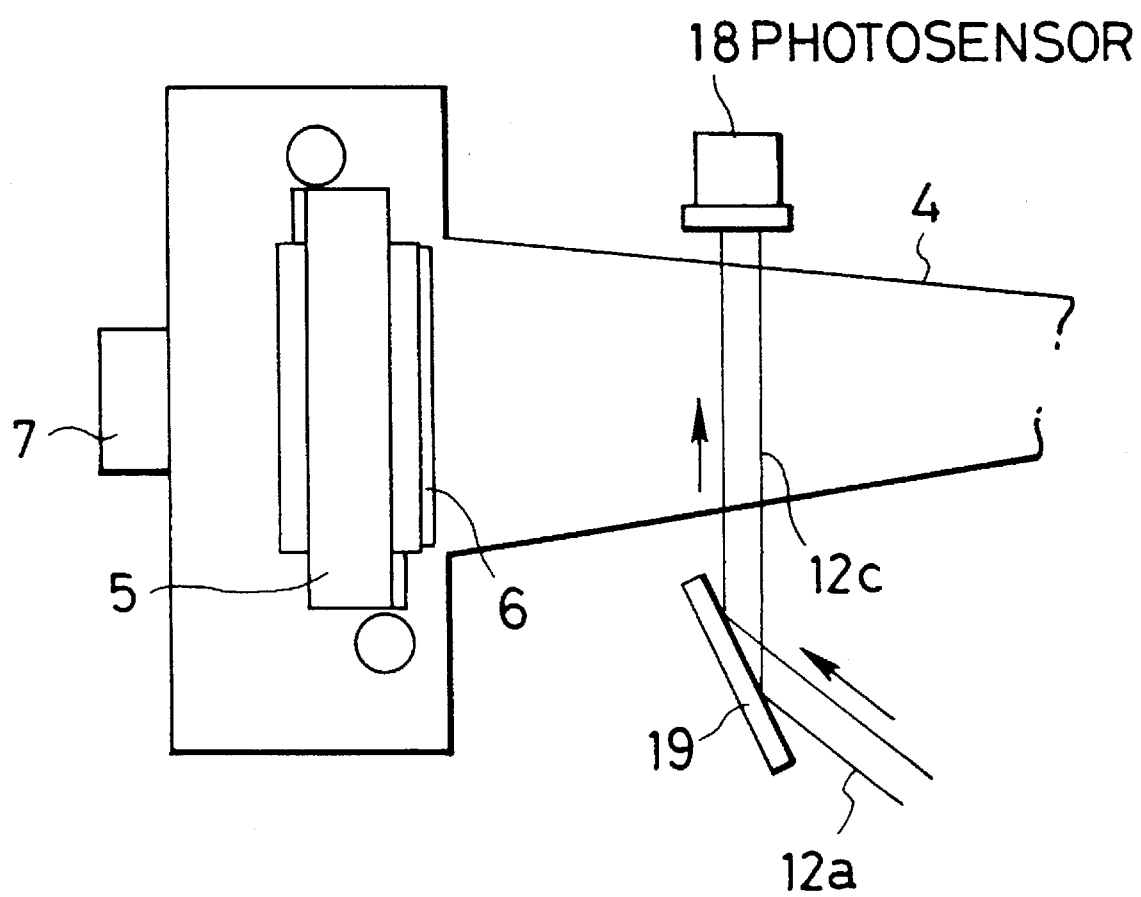
FIG. 2 is a drawing illustrating the configuration of another embodiment of the invention used to measure the relative concentration of particles.

With respect to this method, it is desirable to increase the length of the light path, as this will enable relative concentration to be measured with higher sensitivity and higher precision. It is not essential for the light beam to be reflected off the surface of the crystal oscillator 5 in order to measure relative concentration. Instead, a configuration such as the one shown in FIG. 2 may be used to measure the relative concentration. In the arrangement of FIG. 2 which uses a mirror 19 to reflect the light beam 12a, producing a reflected beam 12c that passes through the measuring cell 4 and impinges on the photosensor 18, the beam that passes through the measuring cell 4 can be located at any desired position on the cell 4.

While a conventional photomultiplier or the like may be used to form the photosensor 18, a photodiode is an ideal choice. The photosensor 18 produces an output corresponding to a scattered light intensity that varies depending on the relative concentration of the particles. This intensity output is normally generated as an electrical signal that is processed, displayed, subjected to precision compensation and the like by means of known specialized electrical circuits, using instruments such as optical power meters, computers, counters, oscillographs, and so forth. After the relative concentration of particles has thus been measured in the measuring cell 4 using an arrangement of light beams, the particles are caused to adhere to the surface of the crystal oscillator 5 by coating the surface with an adhesive 6. Although the crystal oscillator 5 has a set operating frequency, the increase in surface weight resulting from the adhesion of particles reduces the frequency at which the oscillator 5 operates. Since a correlation exists between this frequency variation and the weight of the particles, it is therefore possible to measure the weight of the particles.

As an example of a measurement method, the measurement time can be divided into set periods, and data output obtained for each period. That is, measurement can be easily conducted by dividing the time into periods, for example, by obtaining a data output one hour after the start of measurement, using data output obtained at the end of the next hour as the reference, obtaining a data output at the end of the next hour, and so on.

The adhesive 6 on the crystal oscillator 5 is applied in a very thin layer that ensures that the light beam 12a is sufficiently reflected and, therefore, that measurement of relative concentration is substantially unaffected. Any Substance may be used for the adhesive 6 that can readily adhere particles to the surface of the crystal oscillator 5, and different substances can be used according to the properties of the particles concerned. However, it is desirable to use an adhesive that contains a surfactant or has oily characteristics. A known crystal oscillator may be used as the crystal oscillator 5; it is preferable to use an AT cut type that is little affected by temperature variations, and an oscillator that produces a round fundamental wave. A known oscillating circuit can be used as the oscillating circuit of the crystal oscillator 5, and a frequency counter or the like (not shown) can be used to measure and display particle-induced frequency variations. While any configuration and material can be used for the measuring cell 4 that allows light beam 12a to enter and impinge on the crystal oscillator 5 without any problem, and allows the transmission of reflected light beam 12b or 12c without any problem, it is preferable to use a quartz cell having good transmissivity and a low degree of light frequency dependence. Also, the position of the point of light reflection on the crystal oscillator 5 and the position of the point of light reflection on the mirror 19 can each be arbitrarily set at any position that provides good-quality particle measurement.

The measuring cell 4 does not have to have the configuration shown in FIG. 1, and may be of any configuration that ensures good input/output of light beams 12a, 12b and 12c. The particle property measuring apparatus according to this invention is not limited to the arrangements shown in the drawings but can also be constituted in various other configurations. For example, instead of measuring variation in the concentration of airborne particles, the particles could be water-borne and the concentration measured by measuring the turbidity of the water. Similarly, although FIG. 1 shows the measurement path for measuring particle diameter, particle relative concentration and particle weight arranged in a straight line, while the measurement path has to be a single system, it does not have to be arranged in a straight line but can be bent into a vertical configuration, or any other arrangement can be used that does not impede measurements or adversely affect measurement precision.

The measuring cell 2 does not have to be a single unit. Instead, it may be separated into left and right portions, as indicated in the drawing by vertical broken lines, and the light spot used to measure particle diameter may be focussed in the air, for example. If such an arrangement is used, it is preferable to use a known method to blow clean air in the directions indicated by the broken-line arrows to conduct the particles of interest flow stably into the measuring cell 4 while at the same time ensuring that there is no outside intrusion of unwanted particles and the like into the open portion of the measuring cell 2. When high-precision measurements are required, it is also preferable to use known compensating components and/or electrical circuitry. When it is required to connect a suction pump (not shown) to the exhaust port 7, it is preferable to use a pump that can be set to an arbitrary discharge rate.

Moreover, although in the above description variation in the frequency of the crystal oscillator 5 is measured using an electrical circuit, measurement is not limited to this configuration. For example, an optical configuration may be used, such as the one indicated by broken lines in the drawing in which a semi-reflecting mirror 13a is positioned in the path of the reflected light beam 12b to deflect part of the beam 12b to a photosensor 20, enabling variation in the operating frequency of the crystal oscillator 5 to be measured based on a corresponding variation in the intensity of the received light. In the case of such an arrangement, it is necessary use a photosensor capable of high-speed measurement of light intensity. While a photodiode, photomultiplier or other such device of a known configuration and type having an electrical circuit for high-speed processing of output signals can be used, it is preferable to use a PIN-photodiode or avalanche diode.

The photosensor 18 measures the relative concentration of particles on the basis of low-speed variations in intensity, and therefore uses an electrical circuit that only processes low-speed output signals. Thus, no problem arises between the operation of the photosensors 18 and 20. The outcome of measurements obtained using the photosensor 20 are output as electrical signals that are processed, displayed, compensated and the like by known specialized circuitry and standard counters, oscilloscopes and other such instruments.

Instead of semi-reflecting mirrors, lenses and other such components, conventional optical fiber may be used to conduct light from the light source to the various measurement sections, and to conduct scattered and reflected light to photosensors. When using such an arrangement, a polarizer or other such optical component can be inserted in the light path between the light source 11 and the semi-reflecting mirror 13, for instance, to prevent part of the split beam being reflected back to the light source.

With the measuring apparatus thus configured, all detection sections can be constituted by photosensors. As such, it is possible for the display and other such instrument sections comprised of electrical circuits to be separated from the measurement sections connected by optical fibers. Thus, a configuration may be used comprising the use of optical fibers disposed to conduct light from each detection section to the photosensors 17, 18 and 20, which may be located wherever desired.

Normally the fundamental wave of the crystal oscillator 5 is utilized. However, it is preferable to add an overtone oscillation circuit or multiple wave oscillation circuit, as this increases measurement sensitivity. A configuration is used that enables the crystal oscillator 5 to be readily attached to, and detached from, the measuring cell, and that ensures that all particles which are to be measured are drawn into the measuring cell 4 without the intrusion of outside particles.

While the arrangement of the invention comprises the light source, photosensors, lenses and other components shown in FIG. 1, it is to be understood that the invention is not limited to the illustrated configuration but may use any configuration that does not impede measurements or adversely affect measurement precision. If required, a configuration for measuring the diameter and weight of particles may be used, or one for measuring the diameter and relative concentration of particles.

As described in the foregoing, in accordance with the apparatus of this invention, particle properties are measured based on information contained in light that is scattered, transmitted and/or reflected. This enables real-time, simultaneous, non-contact measurement of the size, relative concentration and weight of particles without adversely affecting particle characteristics. Moreover, the measurement apparatus of this invention can be made small and light, and as measurements are made using light, it does not produce any electrical sparking and therefore can be safely used in combustible gas environments. The apparatus of the invention can be advantageously utilized in factories, buildings, mines and other such fields and locations in which it is necessary to detect variations in the concentration of particles.

What is claimed is:

1. An apparatus for measuring particle properties, comprising a first measurement section having a nozzle-shaped configuration for light incidence, said first measurement section having an inside diameter that does not allow the simultaneous passage of multiple particles; a second measurement section that is connected to the first measurement section and is able to transmit light; a third measurement section that is connected to the second measurement section, said third measurement section having a particle adhesive on its surface and an internal crystal oscillator; intake means for guiding airborne particles to the third measurement section via the first and second measurement sections; a first optical system that projects light at the first measurement section and receives light scattered from particles in the first measurement section; and a second optical system that projects light at the second measurement section and receives light transmitted between particles in the second measurement section; wherein particle size is measured based on intensity of scattered light received by the first measurement section, relative concentration of particles is measured based on intensity of transmitted light received by the second measurement section, and particle weight is measured based on amplitude of variation in operating frequency of the crystal oscillator to which particles have adhered in the third measurement section.

2. An apparatus for measuring particle properties, comprising a first measurement section having a nozzle-shaped configuration for light incidence, said first measurement section having an inside diameter that does not allow the simultaneous passage of multiple particles; a second measurement section that is connected to the first measurement section, said second measurement section having a particle adhesive on its surface and an internal crystal oscillator; intake means for guiding airborne particles to the second measurement section via the first measurement section; and a first optical system that projects light at the first measurement section and receives light scattered from particles in the first measurement section; wherein particle size is measured based on intensity of scattered light received by the first measurement section and particle weight is measured based on amplitude of variation in operating frequency of the crystal oscillator to which particles have adhered in the second measurement section.

3. A measuring apparatus according to claim 1, wherein light from the first optical system is projected at the crystal oscillator and relative concentration of particles is measured based on detection of the light reflected by the second measurement section.

4. A measuring apparatus according to claim 2, wherein light from the first optical system is projected at the crystal oscillator and relative concentration of particles is measured based on detection of the light reflected by the second measurement section.

* * * * *